US011957553B2

(12) United States Patent
Lee et al.

(10) Patent No.: US 11,957,553 B2
(45) Date of Patent: *Apr. 16, 2024

(54) DIAPER PANTS HAVING A WAISTBAND THAT PROVIDES SOFTNESS AND SKIN COMFORT

(71) Applicant: Kimberly-Clark Worldwide, Inc., Neenah, WI (US)

(72) Inventors: Sang Hyun Lee, Guri-si (KR); DongSoo Choi, Seoul (KR); Allyssa Marie Herrmann, Friendswood, TX (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/662,678

(22) Filed: May 10, 2022

(65) Prior Publication Data
US 2022/0257431 A1     Aug. 18, 2022

Related U.S. Application Data

(63) Continuation of application No. 16/488,671, filed as application No. PCT/US2017/019635 on Feb. 27, 2017, now Pat. No. 11,331,229.

(51) Int. Cl.
*A61F 13/49*     (2006.01)
(52) U.S. Cl.
CPC .. *A61F 13/49011* (2013.01); *A61F 13/49061* (2013.01); *A61F 2013/4908* (2013.01)

(58) Field of Classification Search
CPC ............... A61F 13/49; A61F 13/49011; A61F 13/49061; A61F 13/496; A61F 2013/4908
See application file for complete search history.

(56) References Cited

U.S. PATENT DOCUMENTS

| 5,685,874 | A | 11/1997 | Buell et al. |
| 7,955,311 | B2 | 6/2011 | Tanaka et al. |
| 2002/0173768 | A1 | 11/2002 | Elsberg et al. |

(Continued)

FOREIGN PATENT DOCUMENTS

| CN | 1083347 A | 3/1994 |
| CN | 101068519 A | 11/2007 |

(Continued)

*Primary Examiner* — Michele Kidwell
(74) *Attorney, Agent, or Firm* — KIMBERLY-CLARK WORLDWIDE, INC.

(57) ABSTRACT

An absorbent garment that includes a longitudinal axis and a lateral axis. The absorbent garment also includes a front region, a back region and a crotch region, with the crotch region being disposed between the front region and the back region. The crotch region includes an absorbent assembly. The absorbent garment further includes a front panel in the front region, wherein the front panel includes an inner layer, an outer layer and a front longitudinal end; a back panel in the back region, wherein the back panel includes an inner layer, an outer layer and a back longitudinal end. The front panel and the back panel each include a stranded elastic area between their inner and outer layers. The front panel also includes a stretch banded area disposed between the inner and outer layers. The stretch banded area is disposed adjacent the front longitudinal end.

15 Claims, 5 Drawing Sheets

(56) References Cited

U.S. PATENT DOCUMENTS

| | | |
|---|---|---|
| 2004/0005832 A1 | 1/2004 | Neculescu et al. |
| 2004/0006323 A1 | 1/2004 | Hall et al. |
| 2004/0224132 A1 | 11/2004 | Roe et al. |
| 2005/0106971 A1 | 5/2005 | Thomas |
| 2006/0155255 A1 | 7/2006 | McKiernan et al. |
| 2007/0142806 A1 | 6/2007 | Roe et al. |
| 2008/0027406 A1 | 1/2008 | Shirai et al. |
| 2008/0234649 A1 | 9/2008 | Hamall et al. |
| 2010/0049155 A1 | 2/2010 | Soderbergh et al. |
| 2012/0065043 A1 | 3/2012 | Lam et al. |
| 2012/0289922 A1 | 11/2012 | Otsubo et al. |
| 2012/0323204 A1 | 12/2012 | Poole et al. |
| 2013/0281955 A1 | 10/2013 | Kobayashi et al. |
| 2013/0317471 A1 | 11/2013 | Morimoto et al. |
| 2015/0173973 A1 | 6/2015 | Lavon et al. |
| 2016/0100999 A1 | 4/2016 | Hamilton et al. |
| 2016/0166444 A1 | 6/2016 | Finlayson et al. |
| 2016/0175166 A1 | 6/2016 | Zink, II et al. |
| 2017/0105884 A1 | 4/2017 | Wade et al. |
| 2019/0374390 A1 | 12/2019 | Olsson et al. |

FOREIGN PATENT DOCUMENTS

| | | |
|---|---|---|
| CN | 101460124 A | 6/2009 |
| CN | 101641066 A | 2/2010 |
| CN | 201752456 U | 3/2011 |
| CN | 203341926 U | 12/2013 |
| CN | 104302260 A | 1/2015 |
| CN | 104321038 A | 1/2015 |
| CN | 205515213 U | 8/2016 |
| CN | 206837035 U | 1/2018 |
| EP | 1080708 A2 | 3/2001 |
| JP | 2001178772 A | 7/2001 |
| JP | 2008142341 A | 6/2008 |
| JP | 2015051176 A | 3/2015 |
| JP | 2016158799 A | 9/2016 |
| RU | 2248781 C2 | 3/2005 |
| RU | 112038 U1 | 1/2012 |
| WO | 1999060968 A1 | 12/1999 |

DIAPER PANTS HAVING A WAISTBAND THAT PROVIDES SOFTNESS AND SKIN COMFORT

BACKGROUND

Absorbent articles, such as diapers, incontinence garments, training pants, sanitary napkins, panty liners, and the like are well known in the art. These articles, which are often disposable, are capable of absorbing and retaining fluids and other bodily discharges. Some absorbent articles, such as pull-on type absorbent articles, include a central absorbent member and side panels extending from and interconnecting respective front and back regions of the absorbent member forming a waist assembly.

An example of a pull-on absorbent article is a diaper pant; diaper pants are typically worn by babies who are able to stand up, but who are not yet old enough to be toilet trained. Absorbent articles in the diaper pants format typically include a waist assembly (that includes side panels) formed of elastic strands placed between inner and outer layers of a nonwoven material. The elastic strands are typically kept in place by adhesive. These types of waist assemblies may include 20 to 30 high-tension elastic strands that embrace the waist area. The use of the elastic strands in the side panels of the diaper pants allows the side panels to be highly elastic and allows for a wide range of body shapes over which the diaper pant may be donned. The elastic side panels also provide a conforming fit for the wearer.

The high waist area of the waist assembly typically gets stretched the most in use in order to conform to the child's belly/abdomen. If high-tension elastic strands are stretched excessively, they may exert a lot of pressure on the skin which could lead to red-marking on the skin caused by the diaper pant. The extended, high waist area of the diaper pant may have a wrinkled appearance in use; the wrinkled appearance may give an impression of being stuffy and uncomfortable. Further, the known construction of diaper pants does not provide an underwear-like appearance.

There remains a need for a diaper pant that provides a more skin-friendly contact in the high waist area. While providing a more skin-friendly contact, the waist assembly needs to remain very stretchable. There also remains a need for a diaper pant that has fewer wrinkles in the high waist area and, therefore, provides a smoother look around the waist. Further, there remains a need for a diaper pant that provides a more underwear-like appearance in use.

SUMMARY

Significant improvements in appearance, comfort and fit of diaper pants may be achieved using a new construction for the waist assembly of the diaper pant. The waist assembly is typically formed by a front panel and a back panel of the diaper pant. The diaper pants of the invention include a waist assembly having a lower waist area that includes stranded elastics and an upper waist area that includes a discrete, stretch banded area. The stranded elastic area includes an inner material and an outer material in between which the elastic strands are placed. The discrete, stretch banded area is formed by placing a stretchable material (that has stretch in at least one direction; for example, in at least a longitudinal or a lateral direction) against the same outer material used to form the stranded elastic area and then folding the outer material over to cover the other side of the stretch banded material.

In one aspect, the present invention relates to an absorbent garment, such as a diaper pant (for infants and pre-toilet training toddlers), a training pant, a youth pant or an adult incontinence pant. The absorbent garment includes a longitudinal axis and a lateral axis that define the general orientation of the garment. As with known garments, the absorbent garment of the invention has a front region, a back region and a crotch region; the crotch region is disposed between the front region and the back region. The distance or orientation from the front region to the back region defines the longitudinal axis of the garment. The crotch region includes an absorbent assembly. The front region of the absorbent garment includes a front panel; the front panel includes an inner layer, an outer layer and a front longitudinal end. Similarly, the back region of the garment includes a back panel; the back panel includes an inner layer, an outer layer and a back longitudinal end. Each of the front panel and the back panel include a stranded elastic area disposed between the inner layer and the outer layer. The stranded elastic area provides general elasticity to the absorbent garment and contributes to the garment's ability to be pulled upward for donning by the wearer. The stranded elastic area includes elastic strands, such as are known for use in these types of garments. The elastic strands are generally oriented along the lateral axis of the garment. The front panel also includes a stretch banded area disposed between the inner layer and the outer layer. The stretch banded area is disposed adjacent to the longitudinal end of the front panel. The stranded elastic area of the front panel is adjacent to, but discrete from the stretch banded area. The stranded elastic area is closer to the crotch region than the stretch banded area.

In another aspect of the invention, the absorbent garment defines a waist opening in use that is oriented with the lateral axis of the garment. The stretch banded area extends perpendicularly to the longitudinal axis of the garment; meaning, the stretch banded area extends in the direction of the lateral axis and around what is the front region of the waist opening of the garment. In use, the stretch banded area forms a soft "waistband" of the garment. In order for the full circumference of the waist opening to have the "waistband" feature, the back panel includes a stretch banded area disposed between the inner layer and the outer layer. The stretch banded area is disposed adjacent the longitudinal end of the back panel. With this execution, the back panel includes opposed lateral edges and the stretch banded area extends from one lateral edge to the other lateral edge of the back panel. Similarly, the front panel may include opposed lateral edges such that the stretch banded area extends from one lateral edge to the other lateral edge in the front panel.

The stranded elastic areas of the front panel and the back panel may include a plurality of elastic strands disposed perpendicularly to the longitudinal axis. The elastomeric strands may include dry-spun coalesced multifilament spandex elastomeric strands sold under the trade name LYCRA® and available from Invista of Wichita, Kansas, U.S.A. or they may be constructed from vertical filament laminate (VFL) material. The stretch banded area may be formed of a stretchable material selected from films, film laminates, spandex laminates, stretch-bonded laminate (SBL), continuous filament stretch-bonded laminates (CFSBL) and simultaneously aperture and bonded bi-directional elastic laminate (SABBEL).

By providing stretchability to the absorbent garment through the discrete areas of the stretch banded area and the stranded elastic area, the absorbent garments of the invention are more underwear-like in appearance because they have a noticeable waistband area, like underwear. The absorbent garments of the invention also provide a more comfortable fit for the wearer because the stretch banded area forming the waistband is softer and better-conforming. The construction and further aspects of the absorbent garments of the invention are described in more detail herein.

DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

The term "absorbent garment" refers herein to a garment that can be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent garments, including, but not limited to, infant diaper pants, toilet-training pants, youth pants, swim pants, feminine hygiene garments and adult incontinence garments.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements.

The term "carded web" refers herein to a web containing natural or synthetic staple fibers typically having fiber lengths less than about 100 mm. Bales of staple fibers can undergo an opening process to separate the fibers that are then sent to a carding process that separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers can be subject to adhesive processes to bind the fibers together such as by the use of powder adhesives. The carded web can be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films that constitute liquid transfer films, as well as films that do not transfer fluids, such as, but not limited to, barrier films, filled films, breathable films, and oriented films.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams that attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers that can be continuous or discontinuous, are generally smaller than about 0.6 denier, and can be tacky and self-bonding when deposited onto a collecting surface.

The term "nonwoven" refers herein to materials and webs of material that are formed without the aid of a textile weaving or knitting process. The materials and webs of materials can have a structure of individual fibers, filaments, or threads (collectively referred to as "fibers") that can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials that are compliant and that will readily conform to the general shape and contours of the wearer's body.

The term "spunbond" refers herein to small diameter fibers that are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an aspect, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an aspect, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a polymeric material that becomes pliable or moldable above a specific temperature and returns to a solid state upon cooling.

Generally, an absorbent garment having an improved structure is disclosed herein. The improved structure provides a waistband area that is part of an overall waist assembly. The absorbent garments of the invention provide the wearers of the garments with a more comfortable fit because there is less retraction of the elastics in the overall waist assembly. The absorbent garments of the invention have a novel waist assembly structure that includes "territorial" elastics. Conventional absorbent garments have waist assemblies that include either elastic strands by themselves or elastic strands combined with other elastics, but with the elastic strands used throughout the waist assembly. With the absorbent garments of the invention, the waist assembly includes a stretch banded area that is part of the front panel of the garment and may be part of the back panel, too. The stretch banded area is adjacent the longitudinal ends of the front panel and the back panel to form a belt-like waistband. By removing the elastic strands from the longitudinal end area of the front panel, there is less retraction force-resulting in less force against the wearer's skin and, therefore, a lower likelihood of red-marking of the skin.

Figure 1:
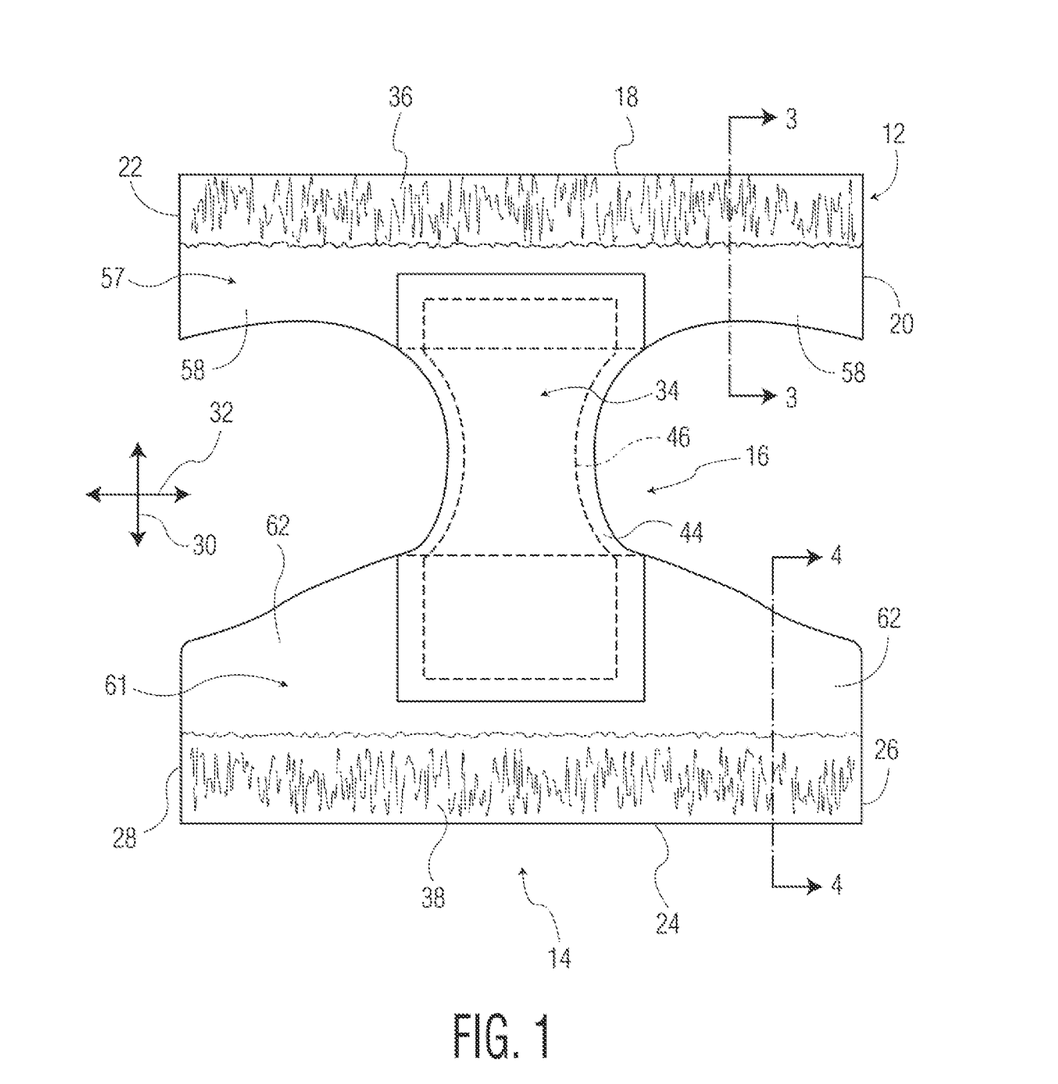
FIG. 1 is a top down view of an absorbent garment of the present disclosure.
Figure 2:
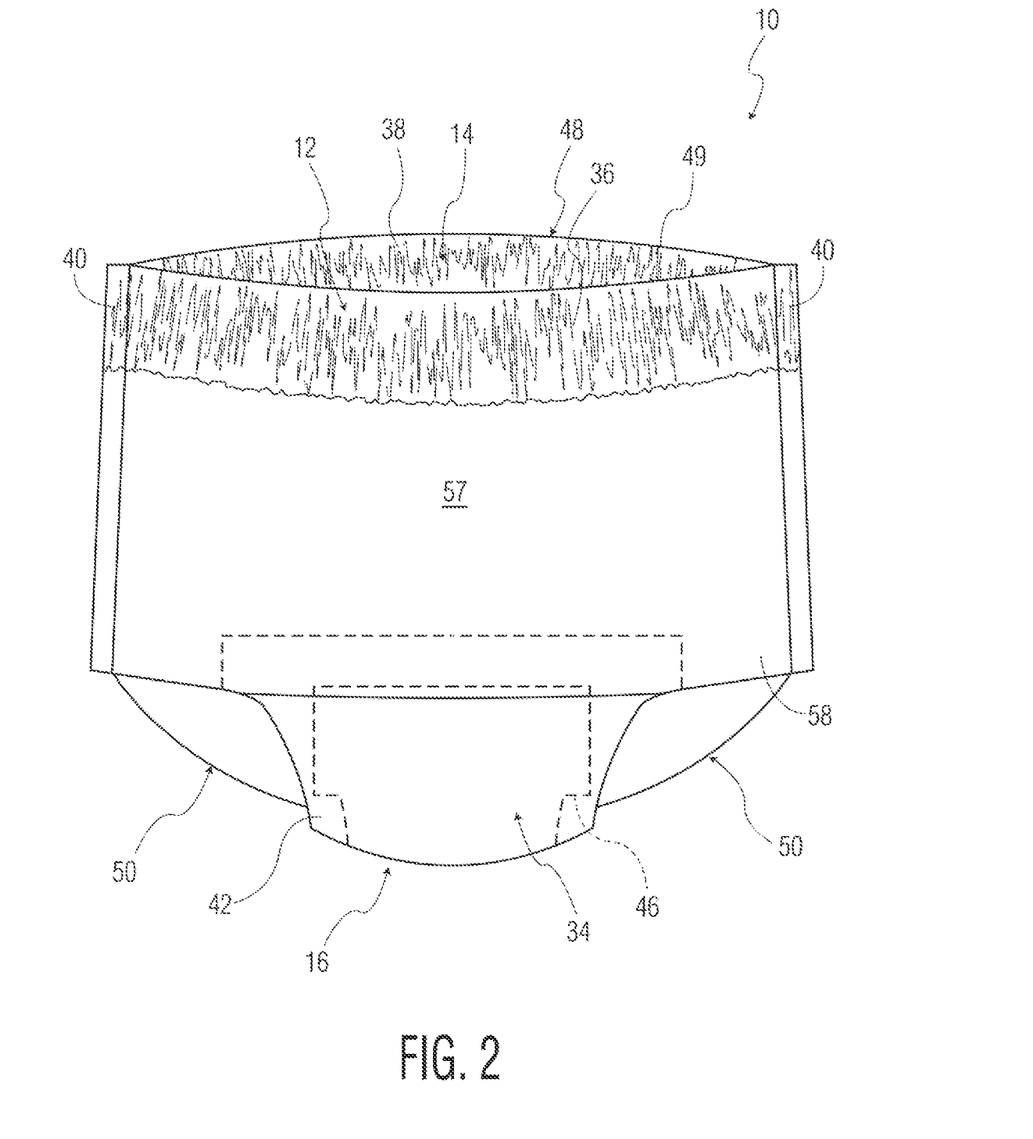
FIG. 2 is a front view of the absorbent garment of FIG. 1, in an assembled condition.

With reference to the drawings, FIGS. 1 and 2 illustrate one suitable aspect of an absorbent garment of the present disclosure in the form of a diaper pant, indicated generally at 10. While the present disclosure will be made in the context of the diaper pant 10, it should be understood that aspects of the present disclosure are applicable to other absorbent garments, such as, for example, toilet-training pants, youth pants, swim pants, feminine hygiene garments and adult incontinence garments. As used herein, the term "absorbent garment" refers to garments that absorb and contain body exudates and that are intended to be discarded after a limited period of use. The garments are not intended to be laundered or otherwise restored for reuse. Put differently, the garments are disposable. The garments can be placed against or in proximity to the body of a wearer to absorb and contain various exudates discharged from the body.

FIG. 1 illustrates the diaper pant 10 in an unfolded and laid flat condition to show an inner surface of the diaper pant that faces the wearer when the diaper pant 10 is worn. The diaper pant 10 has a longitudinal axis (direction) 30 and a lateral axis (direction) 32. Along the longitudinal axis 30, the diaper pant 10 defines a front region 12, a back region 14, and a crotch region 16 extending between and connecting the front region 12 and the back region 14.

In the front region 12, the diaper pant 10 has a front longitudinal end 18 and transversely opposed first and second front side edges 20, 22. A back longitudinal end 24 and transversely opposed first and second back side edges 26, 28 are located in the back region 14 of the diaper pant 10. In the illustrated aspect, the front longitudinal end 18 and the back longitudinal end 24 are straight edges. That is, the front longitudinal end 18 and the back longitudinal end 24 are substantially free from curves, bends, angles, notches or irregularities. It is understood, however, that the front longitudinal end 18 and/or the back longitudinal end 24 can be cut in any suitable shape as is known in the art (e.g., arcuate).

The diaper pant 10 includes a central absorbent assembly, indicated generally at 34, that extends longitudinally from the front region 12 through the crotch region 16 to the back region 14. The central absorbent assembly 34 of the illustrated aspect includes an outer cover 42 (shown in FIG. 2) and a bodyside liner 44 connected to the outer cover 42 in a superposed relation by suitable means such as adhesives, ultrasonic bonds, thermal bonds, pressure bonds, or combinations thereof. An absorbent structure 46 is disposed between the outer cover 42 and the bodyside liner 44.

The front and back regions 12, 14 of the diaper pant 10 include a front panel 57 and a back panel 61, respectively. The front panel 57 and the back panel 61 are interconnected via the absorbent assembly 34. The front panel 57 is a laminate or composite of several materials including an inner layer and an outer layer; the inner layer is closest to the skin of the wearer of the diaper pant 10. The front panel 57 has a front longitudinal end 18. Similarly, the back panel 61 is also a laminate or composite of several materials including an inner layer and an outer layer. The back panel 61 has a back longitudinal end 24. Between the inner layer and outer layer of the front panel 57, there is a stranded elastic area and a stretch banded area 36. Between the inner layer and the outer layer of the back panel 61, there is a stranded elastic area. The stretch banded area 36 of the front panel 57 is disposed adjacent the front longitudinal end 18. The stranded elastic area in the front panel 57 is adjacent to, but discrete from the stretch banded area 36 and the stranded elastic area is closer to the crotch region 16 than the stretch banded area 36. The stretch banded area 36 has the appearance of a waistband, such as would be found on cloth underwear. As shown in FIG. 1, the back panel 61 may also have a stretch banded area 38 between the inner layer and the outer layer; the stretch banded area 38 of the back panel 61 is disposed adjacent the back longitudinal end 24.

As shown in FIG. 1, the front panel 57 includes a pair of laterally-opposed, front side portions 58 extending outward from the lateral center of the absorbent garment. Likewise, the back panel 61 incudes a pair of laterally-opposed, back side portions 62 extending outward from the lateral center of the absorbent garment. As shown in FIG. 2, the front panel 57 is joined to the back panel 61 by a pair of non-refastenable butt (or fin) seams 40 to define a pull-on, pant-like configuration of the diaper pant 10 having a waist opening, indicated at 48, and two leg openings, indicated at 50. More specifically, each front side portion 58 is joined to a respective back side portion 62 via one of the non-refastenable butt seams 40.

With the diaper pant 10 in the pull-on, pant-like configuration, illustrated in FIG. 2, the front region 12 includes the portion of the diaper pant 10 that, when worn, is positioned at least in part on the front of the wearer while the back region 14 includes the portion of the diaper pant 10 that is positioned at least in part on the back of the wearer. The crotch region 16 of the diaper pant 10 includes the portion of the diaper pant 10 that is positioned between the legs of the wearer and covers the lower torso of the wearer. The front and back side portions 58, 62 include the portions of the diaper pant 10 (and more particularly of the front and back regions 12, 14) that, when worn, are positioned on the hips of the wearer. As shown in FIG. 2, the film elastic area 36 of the front panel 57 and the film elastic area 38 of the back panel 61 cooperatively define the waist opening 48 of the diaper pant 10 that is configured to fully encircle the waist of the wearer.

The central absorbent assembly 34 is configured to contain and/or absorb exudates discharged from the wearer. The outer cover 42 suitably includes a material which is substantially liquid impermeable. The outer cover 42 can be a single layer of liquid impermeable material, but more suitably includes a multi-layered laminate structure in which at least one of the layers is liquid impermeable. For instance, the outer cover 42 can include a liquid permeable outer layer and a liquid impermeable inner layer that are suitably joined together by an adhesive, ultrasonic bonding, thermal bonding, pressure bonding, or combinations thereof. Suitable adhesives can be applied continuously or intermittently as beads, a spray, parallel swirls, or the like. The liquid permeable outer layer can be any suitable material, including materials that provide a generally cloth-like texture. The outer layer can also be made of those materials of which the liquid permeable bodyside liner 44 is made. While it is not a necessity for the outer layer to be liquid permeable, it is suitable that it provides a relatively cloth-like texture to the wearer.

The inner layer of the outer cover 42 can be both liquid and vapor impermeable, or it can be liquid impermeable and vapor permeable. The inner layer can be manufactured from a thin plastic film, although other flexible liquid impermeable materials can also be used. The inner layer, or the liquid impermeable outer cover 42 when a single layer, prevents waste material from wetting articles, such as bed sheets and clothing, as well as the wearer and caregiver.

If the outer cover 42 is a single layer of material, it can be embossed and/or matte finished to provide a more cloth-like appearance. As earlier mentioned, the liquid impermeable material can permit vapors to escape from the interior of the absorbent garment, while still preventing liquids from passing through the outer cover 42. One suitable "breathable" material is composed of a microporous polymer film or a nonwoven fabric that has been coated or otherwise treated to impart a desired level of liquid impermeability. It is also contemplated that the outer cover 42 can be stretchable, and more suitably elastic. In particular, the outer cover 42 is suitably stretchable and more suitably elastic in at least the transverse (lateral), or circumferential direction of the pant 10. In other aspects the outer cover 42 can be stretchable, and more suitably elastic, in both the transverse (lateral) and the longitudinal direction.

The liquid permeable bodyside liner 44 is illustrated as overlying the outer cover 42 and absorbent structure 46, and can, but need not, have the same dimensions as the outer cover 42. The bodyside liner 44 is suitably compliant, soft feeling, and non-irritating to the wearer's skin. The bodyside liner 44 is also sufficiently liquid permeable to permit liquid body exudates to readily penetrate through its thickness to the absorbent structure 46. Further, the bodyside liner 44 can be less hydrophilic than the absorbent structure 46 to present a relatively dry surface to the wearer and permit liquid to readily penetrate through its thickness. The hydrophilic/hydrophobic properties can be varied across the length, width and/or depth of the bodyside liner 44 and absorbent structure 46 to achieve the desired wetness sensation or leakage performance.

The bodyside liner 44 can be manufactured from a wide selection of web materials, such as porous foams, reticulated foams, apertured plastic films, woven and nonwoven webs, or a combination of any such materials. For example, the bodyside liner 44 can include a meltblown web, a spunbonded web, or a bonded-carded-web composed of natural fibers, synthetic fibers or combinations thereof. The bodyside liner 44 can be composed of a substantially hydrophobic material, and the hydrophobic material can optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 44 or can be selectively applied to particular sections of the bodyside liner 44, such as the medial section along the longitudinal center line.

The bodyside liner 44 can also be stretchable, and, more suitably, it can be elastomeric. In particular, the bodyside liner 44 is suitably stretchable and more suitably elastomeric in at least the lateral or circumferential direction 32 of the diaper pant 10. In other aspects, the bodyside liner 44 can be stretchable, and more suitably elastomeric, in both the lateral direction 32 and the longitudinal direction 30.

The absorbent structure 46 is suitably compressible, conformable, non-irritating to a wearer's skin, and capable of absorbing and retaining liquids and certain body wastes. For example, the absorbent structure 46 can include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

The materials can be formed into a web structure by employing various conventional methods and techniques. For example, the absorbent structure 46 can be formed by a dry-forming technique, an air forming technique, a wet-forming technique, a foam-forming technique, or the like, as well as combinations thereof. Furthermore, the absorbent structure 46 can itself encompass multiple layers in a Z-direction (e.g., thickness) of the absorbent structure 46. Such multiple layers can take advantage of differences in absorbent capacity, such as by placing a lower absorbent capacity material layer closer to the bodyside liner 44 and a higher absorbent capacity material closer to the outer cover 42. Likewise, discrete portions of a single-layered absorbent structure can encompass higher capacity absorbents, and other discrete portions of the structure can encompass lower capacity absorbents.

Superabsorbent material is suitably present in the absorbent structure 46 in an amount of from about 0 to about 100 weight percent based on total weight of the absorbent structure 46. The absorbent structure 46 can suitably have a density within the range of about 0.10 to about 0.60 grams per cubic centimeter. Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid.

The absorbent structure 46 can alternatively include a coform material. The term "coform material" generally refers to composite materials including a mixture or stabilized matrix of thermoplastic fibers and a second non-thermoplastic material. As an example, coform materials are made by a process in which at least one meltblown die head is arranged near a chute through which other materials are added to the web while it is forming. Such other materials can include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers can be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene.

In one suitable aspect, the absorbent structure 46 is stretchable so as not to inhibit the stretchability of other components to which the absorbent structure can be adhered, such as the outer cover 42 and the bodyside liner 44. After being formed or cut to a desired shape, the absorbent structure 46 can be wrapped or encompassed by a suitable wrap (not shown) that aids in maintaining the integrity and shape of the absorbent structure 46.

The absorbent assembly 34 can also include a surge management layer (not shown) located adjacent the absorbent structure 46 (e.g., between the absorbent structure 46 and the bodyside liner 44) to help decelerate and diffuse surges or gushes of liquid that can be rapidly introduced into the absorbent structure 46 of the diaper pant 10 by the wearer. Desirably, the surge management layer can rapidly accept and temporarily hold the liquid prior to releasing the liquid into the storage or retention portions of the absorbent structure 46. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, II et al., the entire disclosures of which are hereby incorporated by reference.

The absorbent assembly 34 can also include a pair of containment flaps (not shown) that extend longitudinally along the absorbent assembly 34 and are adapted to provide a barrier to the lateral flow of body exudates as is known in the art. The containment flaps can be connected to the bodyside liner 44 or other components of the absorbent assembly 34. Suitable configurations of the containment flaps are described, for example, in U.S. Pat. No. 5,599,338 issued Feb. 4, 1997, to K. Enloe, the entirety of which is incorporated herein by reference.

Figure 3:
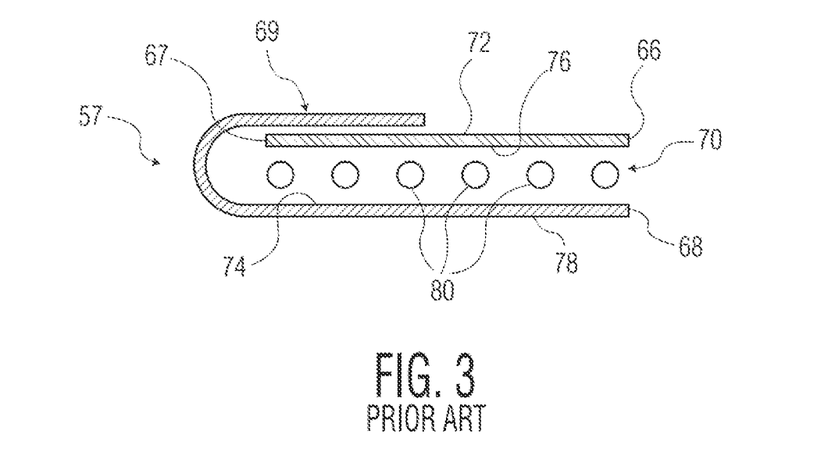
FIG. 3 is a cross-sectional view of a conventional (prior art) absorbent garment having the same, general structure as the absorbent garment of FIG. 1 taken along line "3-3" in FIG. 1.

With reference to FIG. 3, the structure used to form the front panel 57 in a prior art absorbent garment includes a multi-layer construction including an inner or body-facing layer 66, an outer or garment-facing layer 68, and an elastic layer 70 disposed between the inner layer 66 and the outer layer 68. The inner layer 66 and the outer layer 68 each include, respectively, a body-facing side 72, 74 and a garment-facing side 76, 78. The garment-facing side 76 of the inner layer 66 is connected to the body-facing side 74 of the outer layer 68 by suitable means such as adhesives, ultrasonic bonds, thermal bonds, pressure bonds, or combinations thereof. In the illustrated aspect, an upper portion 69 of the outer layer 68 is folded over a top edge 67 of the inner layer 66. The upper portion 69 is connected to the body-facing side 72 of the inner layer 66 to close the top edge 49 of the waist opening 48 (FIG. 2), and enclose the elastic layer 70 between the inner layer 66 and the outer layer 68.

The inner layer 66 is typically constructed from a non-apertured nonwoven material. Suitable nonwovens include single layer nonwovens, such as spunbond webs, and nonwoven laminates. In one suitable aspect, the inner layer 66 includes a spunbond/spunbond/spunbond ("SSS") laminate. In another suitable aspect, the inner layer 66 includes at least one meltblown layer positioned between two or more spunbond layers to form a spunbond/meltblown/spunbond ("SMS") laminate. In one particular aspect, the inner layer 66 includes a spunbond/spunbond/meltblown/meltblown/spunbond laminate ("SSMMS"). The nonwoven laminate can have other configurations and possess any desired number of meltblown and spunbond layers, such as spunbond/meltblown/meltblown/spunbond laminates ("SMMS"), spunbond/meltblown laminates ("SM"), etc. In addition to or as an alternative to meltblown and spunbond webs, a variety of other nonwoven webs can also be used to form the inner layer 66 including, for example and without limitation, through-air bonded carded webs, thermally bonded carded webs, wet-laid webs, coform webs, and hydraulically entangled webs.

The inner layer 66 may be liquid-impermeable and vapor permeable. That is, the inner layer 66 permits vapors to escape from the interior of the absorbent garment, while still preventing liquids from passing through the inner layer 66. The inner layer 66 can be treated or otherwise processed to impart a desired level of liquid impermeability to the inner layer 66.

The elastic layer 70 is attached to at least one of the inner layer 66 and the outer layer 68 to impart a desired level of elasticity to the front panel 57. The elastic layer 70 may be attached to the inner layer 66 and/or the outer layer 68 by any suitable means including, for example, adhesives. The elastic layer 70 may be stretched and then adhered to one or both of the inner layer 66 and the outer layer 68, or adhered to one or both of the inner layer 66 and the outer layer 68 when the layers 66, 68 are in a gathered state to impart a desired level of elasticity to the front panel 57. In other aspects, the elastic layer 70 may be adhered to one or both of the inner layer 66 and the outer layer 68, and then elasticized or shrunk, for example with the application of heat, such that elastic retractive forces are imparted to the front panel 57.

The elastic layer 70 may be formed of a variety of suitable elastic materials, including strands or ribbons of natural rubber, synthetic rubber, or thermoplastic elastomeric polymers. In the aspect shown in FIG. 3, the elastic layer 70 includes a plurality of elastomeric strands 80 extending in the lateral direction 32 (FIG. 1) or circumferential direction (FIG. 2) of the diaper pant 10. In one suitable aspect, the elastomeric strands 80 include dry-spun coalesced multifilament spandex elastomeric strands sold under the trade name LYCRA® and available from Invista of Wichita, Kansas, U.S.A. Other suitable materials from which the elastic layer 70 may be constructed include vertical filament laminate (VFL) materials, an example of which is described in U.S. Pat. No. 6,916,750 to Thomas et al., which is hereby incorporated by reference.

The outer layer 68 is vapor permeable, and may be liquid permeable or liquid impermeable. The outer layer 68 may be constructed from an apertured nonwoven, such as a single layer nonwoven or a nonwoven laminate. In one suitable aspect, the outer layer 68 includes a spunbond/spunbond/spunbond ("SSS") laminate. In another suitable aspect, the outer layer 68 includes at least one meltblown layer positioned between two or more spunbond layers to form a spunbond/meltblown/spunbond ("SMS") laminate. In one aspect, the outer layer 68 includes a spunbond/spunbond/meltblown/meltblown/spunbond laminate ("SSMMS"). The nonwoven laminate can have other configurations and possess any desired number of meltblown and spunbond layers, such as spunbond/meltblown/meltblown/spunbond laminates ("SMMS"), spunbond/meltblown laminates ("SM"), etc. In addition to or as an alternative to meltblown and spunbond webs, a variety of other nonwoven webs can also be used to form the outer layer 68 including, for example and without limitation, through-air bonded carded webs, thermally bonded carded webs, wet-laid webs, coform webs, and hydraulically entangled webs.

The inner layer 66 and the outer layer 68 are joined together in face-to-face relationship by suitable means such as adhesives, ultrasonic bonding, thermal bonding, pressure bonding, or combinations thereof. Suitable adhesives, which can be applied continuously or intermittently as beads, a spray, parallel swirls, or the like, include elastomeric adhesives (i.e. materials capable of at least 75% elongation without rupture), such as aqueous-based styrene butadiene adhesives, neoprene, polyvinyl chloride, vinyl copolymers, polyamides, and ethylene vinyl terpolymers.

Figure 4:
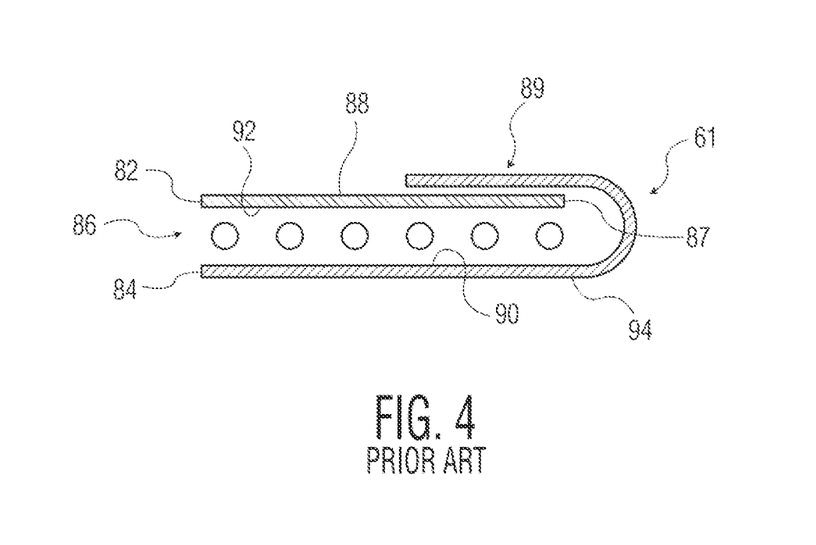
FIG. 4 is a cross-sectional view of a conventional (prior art) absorbent garment having the same, general structure as the absorbent garment of FIG. 1 taken along line "4-4" in FIG. 1.

Referring to FIG. 4, the structure used to form the back panel 61 of a prior art absorbent garment has the same construction and configuration as the front panel 57. That is, the back panel 61 includes a multi-layer construction including an inner or body-facing layer 82, an outer or garment-facing layer 84, and an elastic layer 86 disposed between the inner layer 82 and the outer layer 84. The inner layer 82 and the outer layer 84 each include, respectively, a body-facing side 88, 90 and a garment-facing side 92, 94. In the aspect illustrated in FIG. 4, an upper portion 89 of the outer layer 84 is folded over a top edge 87 of the inner layer 82. The upper portion 89 is connected to the body-facing side 88 of the inner layer 82 to close the top edge 49 of the waist opening 48 (FIG. 2), and enclose the elastic layer 86 between the inner layer 82 and the outer layer 84. The layers 82, 84 and 86 of the back panel 61 may be constructed of the same materials as the layers 66, 68 and 70 of the front panel 57 described above with reference to FIG. 3.

Figure 6:
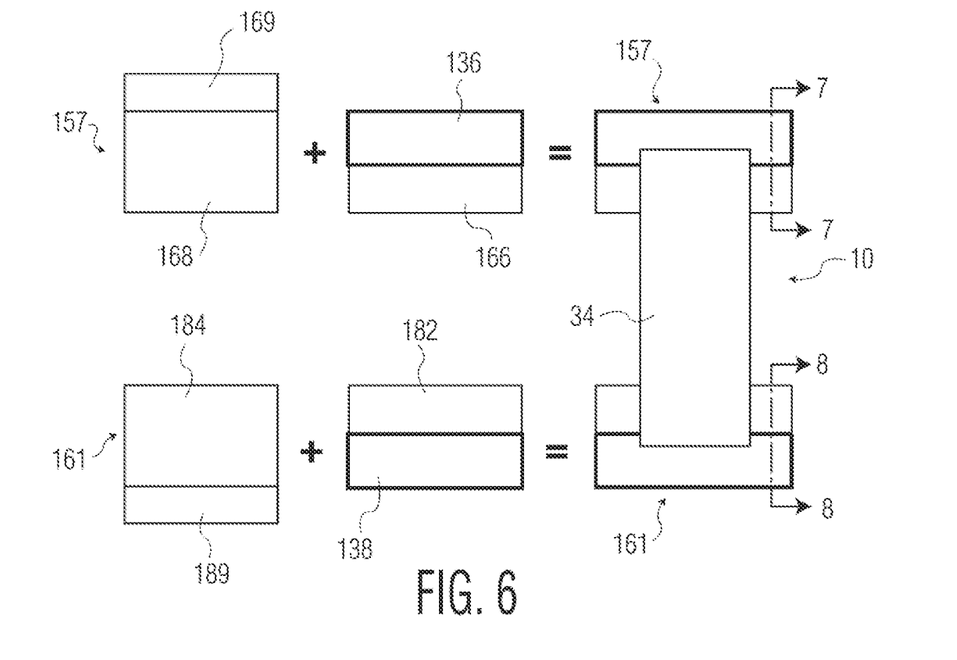
FIG. 6 is a schematic illustration of the assembly of an absorbent garment of the present invention with a film elastic area in each of the front and back panels.
Figure 7:
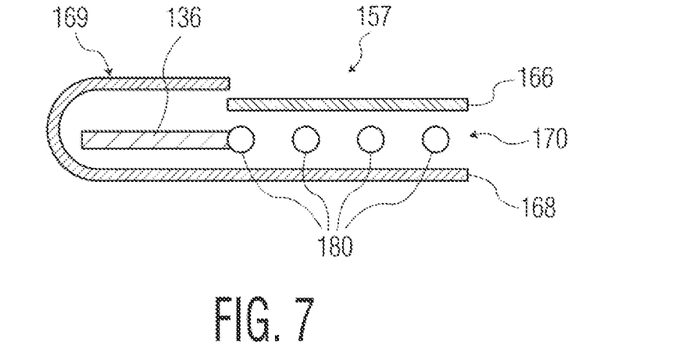
FIG. 7 is a cross-sectional view of the absorbent garment of FIG. 6 taken along line "7-7" in FIG. 6.
Figure 8:
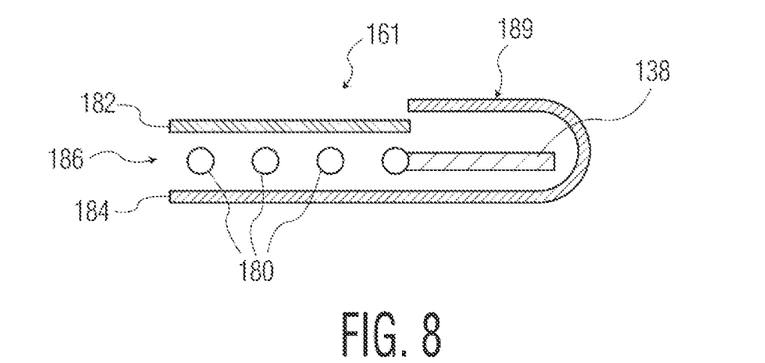
FIG. 8 is a cross-sectional view of the absorbent garment of FIG. 6 taken along line "8-8" in FIG. 6.

FIGS. 6-8 illustrate aspects of the present invention. As illustrated in FIGS. 6-8, the absorbent garment 10 includes a front panel 157 in the front region 12 and a back panel 161 in the back region 14. The front panel 157 includes an inner layer 166, an outer layer 168, a stretch banded area 136 and a stranded elastic layer 170 that includes elastomeric strands 180. The back panel 161 includes an inner layer 182, an outer layer 184, a stretch banded area 138 and an elastic layer 186 that can include elastomeric strands 180. The inner layers 166, 182 are affixed to the outer layers 168, 184, respectively, with the stretch banded areas 136, 138 and the elastic layers 170, 186 sandwiched therebetween. These are typically affixed to each other with adhesive, although any suitable attachment means can be used. Strands 180 are typically disposed generally perpendicular to the longitudinal axis and generally parallel to the lateral axis. As shown in FIG. 7, an upper portion 169 of the outer layer 168 is folded over the stretch banded area 136. As shown in FIG. 8, an upper portion 189 of the outer layer 184 is folded over the stretch banded area 138. The stretch banded areas 136, 138 may be formed of films, film laminates and apertured elastic films, examples of which are described in U.S. Pat. No. 7,803,244 issued Sep. 28, 2010 to Siqueira et al., and U.S. Pat. No. 8,361,913 issued Jan. 29, 2013 to Siqueira et al., both of which are hereby incorporated by reference, and other elastic laminates such as single- and dual-faced spandex laminates, stretch-bonded laminates (SBL), and continuous filament stretch-bonded laminates (CFSBL), simultaneously aperture and bonded bi-directional elastic laminate (SABBEL), examples of which are described in U.S. Pat. No. 5,385,775 issued Jan. 31, 1995 to Wright; U.S. Pat. No. 6,057,024 issued May 2, 2000 to Mleziva et al.; and U.S. Pat. No. 6,969,441 issued Nov. 29, 2005 to Welch et al., all of which are hereby incorporated by reference. The elastomeric strands 180 may be formed of the same materials as described previously herein for elastomeric strands 80. The elastic materials can be stretched and bonded to a substrate, bonded to a gathered substrate, or bonded to a substrate and then elasticized or shrunk, for example, with the application of heat, such that elastic retractive forces are imparted to the substrate.

Figure 5:
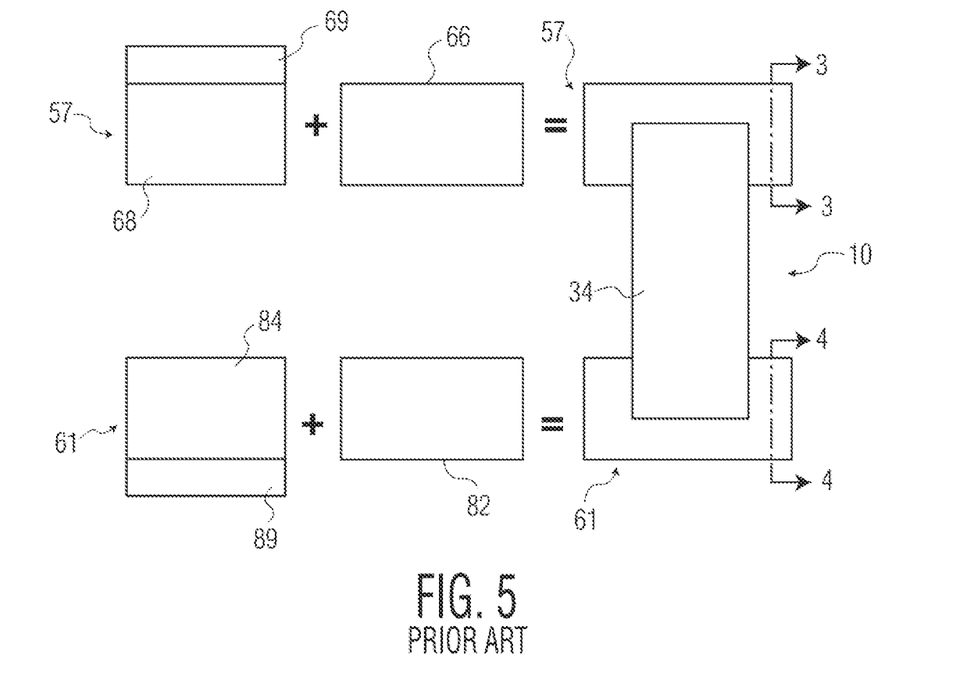
FIG. 5 is a schematic illustration of the assembly of a conventional (prior art) absorbent garment.

FIGS. 5-8 schematically illustrate the general arrangement of components in the absorbent garments 10. FIGS. 5 and 6 are simplified to demonstrate the concept and do not include various elements of the absorbent garments 10. FIG. 5 illustrates the arrangement of elements in a conventional absorbent garment, diaper pant 10. Outer layers 68, 84 are added to inner layers 66, 82 (along with elastics and adhesive, not shown) to form front and back panels 57, 61. The front and back panels 57, 61 are then affixed to a central absorbent assembly 34 to form the diaper pant 10. The upper portion 69 is folded over the inner layer 66, as is the upper portion 89 folded over the inner layer 82. The central absorbent assembly 34 includes the other components of a bodyside liner 44, absorbent structure 46 and outer cover 42 as described herein. Cross sections of conventional panels 57, 61 are illustrated in FIGS. 3 and 4, respectively.

FIG. 6 illustrates the arrangement of elements in the absorbent garment, a diaper pant 10 of the present disclosure. In FIGS. 6-8, both of the front and back panels 157, 161 are substituted for the respective front and back panels 57, 61 of the absorbent article 10 of FIGS. 3-5. Outer layers 168, 184 are added to the combination of stretch banded areas 136, 138 and inner layers 166, 182, respectively, to form front and back panels 157, 161. The inner layers 166, 182 include stranded elastic areas that are not shown in FIG. 6. The upper portion 169 is folded over the stretch banded area 136, as is the upper portion 189 folded over the stretch banded area 138. The front and back panels 157, 161 are then affixed to a central absorbent assembly 34 to form the diaper pant 10. The central absorbent assembly 34 includes the other components of a bodyside liner 44, absorbent structure 46 and outer cover 42 as described herein. Cross sections of front and back panels 157, 161 of the present disclosure are illustrated in FIGS. 7 and 8. Again, one or both of the front and back panels 157, 161 illustrated in FIGS. 7 and 8 may be used to form a diaper pant 10 of the invention. If only the front panel 157 (including stretch banded area 136) is used to form the diaper pant 10, the structure shown in FIG. 7 is present and the back panel 161 will remain as illustrated in FIG. 4. The stretch banded area 136 is disposed adjacent the longitudinal end 18 of the front panel 157 and the stranded elastic area 170 is adjacent and discrete from the stretch banded area 136. The stranded elastic area 170 is closer to the crotch region than the stretch banded area 136. When the back panel 161 also includes the stretch banded area 138 (as shown in FIG. 6 and FIG. 8), the stretch banded area 138 is disposed adjacent the longitudinal end 24 of the back panel 161 and the stranded elastic area 186 is adjacent and discrete from the stretch banded area 138. The stranded elastic area 186 is closer to the crotch region than the stretch banded area 138.

In the interests of brevity and conciseness, any ranges of values set forth in this disclosure contemplate all values within the range and are to be construed as support for claims reciting any sub-ranges having endpoints that are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by references, the meaning or definition assigned to the term in this written document shall govern.

While particular aspects of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. An absorbent garment comprising:
   a longitudinal axis and a lateral axis;
   a front region, a back region, a crotch region, the crotch region being disposed between the front region and the back region, and the crotch region including an absorbent assembly;
   a front panel in the front region, wherein the front panel includes an inner layer, an outer layer and a front longitudinal end;
   a back panel in the back region, wherein the back panel includes an inner layer, an outer layer and a back longitudinal end;
   a stranded elastic area disposed between the inner layer and the outer layer in the front panel and in the back panel; and
   a stretch banded area disposed between the inner layer and the outer layer in the front panel where a portion of the front panel outer layer is folded over the stretch banded area and affixed to the front panel inner layer, the stretch banded area being disposed adjacent the longitudinal end of the front panel with the stranded elastic area disposed closer to the crotch region than the stretch banded area,
   wherein the stretch banded area is discrete from the stranded elastic area such that the stretch banded area is free of elastomeric strands, and
   wherein the stretch banded area is formed of an elastomeric film material.

2. The garment of claim 1, wherein the stretch banded area is formed of a single-faced elastomeric film material.

3. The garment of claim 1, wherein the stretch banded area is formed of an apertured elastomeric film material.

4. The garment of claim 1, wherein the stretch banded area extends perpendicularly to the longitudinal axis.

5. The garment of claim 1, further including a stretch banded area disposed between the inner layer and the outer layer in the back panel where a portion of the back panel outer layer is folded over the stretch banded area and affixed to the back panel inner layer, the stretch banded area being disposed adjacent the longitudinal end of the back panel with the stranded elastic area disposed closer to the crotch region than the stretch banded area, and wherein the stretch banded area is discrete from the stranded elastic area.

6. The garment of claim 5, wherein the back panel includes opposed lateral edges, and wherein the stretch banded area in the back panel extends from one lateral edge to the other lateral edge.

7. The garment of claim 5, wherein the stretch banded area of the back panel formed of an elastomeric film material.

8. The garment of claim 7, wherein the stretch banded area is formed of a single-faced elastomeric film material.

9. The garment of claim 7, wherein the stretch banded area is formed of an apertured elastomeric film material.

10. The garment of claim 5, wherein the stretch banded area of the back panel consists of the back panel inner layer, the back panel outer layer, and the elastomeric film material.

11. The garment of claim 1, wherein the front panel includes opposed lateral edges, and wherein the stretch banded area in the front panel extends from one lateral edge to the other lateral edge.

12. The garment of claim 1, wherein the stranded elastic area in the front panel includes a plurality of elastic strands that are disposed perpendicularly to the longitudinal axis.

13. The garment of claim 1, wherein the stranded elastic area in the back panel includes a plurality of elastic strands that are disposed perpendicularly to the longitudinal axis.

14. The garment of claim 1, wherein the stretch banded area is formed of a material selected from films, laminated films, spandex laminates, stretch-bonded laminate (SBL), continuous filament stretch-bonded laminates (CFSBL) and simultaneously aperture and bonded bi-directional elastic laminate (SABBEL).

15. The garment of claim 1, wherein the stretch banded area consists of the front panel inner layer, the front panel outer layer, and the elastomeric film material.

* * * * *